United States Patent
Mezger

(10) Patent No.: US 9,427,360 B2
(45) Date of Patent: Aug. 30, 2016

(54) HEMOSTATIC FABRIC

(76) Inventor: W. Jerry Mezger, Coto de Caza, CA (US)

( * ) Notice: Subject to any disclaimer, the term of this patent is extended or adjusted under 35 U.S.C. 154(b) by 59 days.

(21) Appl. No.: 13/289,453

(22) Filed: Nov. 4, 2011

(65) Prior Publication Data

US 2012/0116280 A1    May 10, 2012

Related U.S. Application Data

(60) Provisional application No. 61/410,191, filed on Nov. 4, 2010.

(51) Int. Cl.
*A61F 13/00* (2006.01)

(52) U.S. Cl.
CPC ... *A61F 13/00008* (2013.01); *A61F 13/00034* (2013.01); *A61F 2013/00463* (2013.01); *A61F 2013/00472* (2013.01)

(58) Field of Classification Search
CPC ............. A61F 13/00; A61F 13/00004; A61F 13/00008; A61F 13/00034; A61F 2013/00089; A61F 2013/00463
USPC ................. 602/41–44, 48; 424/443, 445–447
See application file for complete search history.

(56) References Cited

U.S. PATENT DOCUMENTS

| | | | |
|---|---|---|---|
| 3,328,259 A | 6/1967 | Anderson | |
| 4,192,299 A | 3/1980 | Sabatano | |
| 4,390,519 A | 6/1983 | Sawyer | |
| 4,453,939 A | 6/1984 | Zimmerman et al. | |
| 4,606,337 A | 8/1986 | Zimmermann et al. | |
| 4,616,644 A | 10/1986 | Saferstein et al. | |
| 5,069,899 A * | 12/1991 | Whitbourne et al. | 424/56 |
| 5,800,372 A | 9/1998 | Bell et al. | |
| 5,902,608 A | 5/1999 | Read et al. | |
| 6,638,296 B2 | 10/2003 | Levinson | |
| 6,762,336 B1 | 7/2004 | MacPhee et al. | |
| 6,891,077 B2 | 5/2005 | Rothwell et al. | |
| 6,897,348 B2 | 5/2005 | Malik | |
| 2007/0160653 A1 | 7/2007 | Fischer et al. | |
| 2007/0207186 A1* | 9/2007 | Scanlon et al. | 424/424 |
| 2009/0053288 A1* | 2/2009 | Eskridge et al. | 424/447 |
| 2010/0228174 A1* | 9/2010 | Huey et al. | 602/44 |

FOREIGN PATENT DOCUMENTS

| | | |
|---|---|---|
| WO | WO/97/28832 | 8/1997 |
| WO | WO/99/59647 | 11/1999 |

OTHER PUBLICATIONS

Hong et al. Thromb Haemost, Jul. 1999:82(1) pp. 58-64.
TH Fischer et al., Biomed Mater Res Part B: Appl Biomater 91B:pp. 381-389, 2009.
Kim TS Invest Radiol 33(7): 1998 pp. 407-410, (printed in 5 pages).
Thor et al. Biomat 28 (2007), pp. 966-974.

* cited by examiner

*Primary Examiner* — Keri J Nelson
(74) *Attorney, Agent, or Firm* — Knobbe, Martens, Olson & Bear, LLP

(57) ABSTRACT

Disclosed herein are hemostatic fabrics that include agents, including metal fibers or powders, that can control bleeding and contribute to faster wound healing.

12 Claims, 1 Drawing Sheet

HEMOSTATIC FABRIC

CROSS-REFERENCE TO RELATED APPLICATIONS

This application claims priority under 35 U.S.C. §119(e) as a nonprovisional of U.S. Prov. Pat. App. 61/410,191 filed on Nov. 4, 2010, which is hereby incorporated by reference in its entirety.

BACKGROUND OF THE INVENTION

1. Field of the Invention

The invention is generally directed to fabrics that include agents that can control bleeding and contribute to faster wound healing.

2. Description of the Related Art

Many products and devices have been developed to control bleeding and yet there remains a significant unmet need for materials that can be applied to sites of hemorrhage to control bleeding. In 2007 the Center for Disease Control reported nearly 124,000 accidental deaths in the U.S. and uncontrolled bleeding is a major morbidity and mortality factor. After a traumatic injury, hemorrhage is responsible for over 35% of pre-hospital deaths and over 40% of deaths within the first 24 hours (Kauvar, D. S., Lefering, R., and Wade, C. E; *J Trauma* 2006).

The standard of care is frequently the application of a tourniquet to control "compressible" bleeding and then gauze to control the residual "noncompressible" bleeding. However, continued blood loss through gauze is a major contributor to morbidity and mortality.

The prior art is replete with patents directed to various forms of bandages. Several of these methods include articles such as bandages supplemented with substances that chemically accelerate the body's natural clotting processes. Examples of such articles include the following, all of which are hereby incorporated by reference in their entireties.

U.S. Pat. No. 3,328,259 to Anderson discloses a bandage or wound dressing that incorporates polymers such as sodium carboxymethyl cellulose, hydroxyethyl cellulose, polyoxyethylene, polyvinylpyrrolidone, etc.

U.S. Pat. No. 4,192,299 to Sabatano discloses a bandage that includes a packet containing an antiseptic substance.

U.S. Pat. No. 4,390,519 to Sawyer discloses a bandage in the form of a sponge and containing collagen or a collagen-like substance.

U.S. Pat. No. 4,453,939 to Zimmerman et al. discloses a composition useful as a wound dressing and made from a combination of collagen, fibrinogen and thrombin.

U.S. Pat. No. 4,606,337 to Zimmerman et al. discloses a resorptive sheet for closing and treating wounds, and composed of a glycoprotein matrix that contains fibrinogen and thrombin.

U.S. Pat. No. 4,616,644 to Saferstein et al. discloses an adhesive bandage that includes high molecular weight polyethylene oxide as a hemostatic agent.

U.S. Pat. No. 5,800,372 to Bell et al. discloses a dressing made from an absorbent polymer and includes microfibrillar collagen.

U.S. Pat. No. 5,902,608 to Read et al. discloses surgical aids such as bandages, gauzes, sutures, and the like, that contain fixed-dried blood cells that express platelet-derived growth factors.

U.S. Pat. No. 6,638,296 to Levinson discloses a bandage that includes a pad containing glucosamine or a glucosamine derivative.

U.S. Pat. No. 6,762,336 and International Patent Application Publication No. WO/99/59647 to MacPhee et al. discloses a multilayer bandage that includes a thrombin layer 5 sandwiched between two fibrinogen layers.

U.S. Pat. No. 6,897,348 to Malik discloses an adhesive bandage that contains an antimicrobial agent and a hemostatic agent (e.g., chitosan, niacinamide, or ascorbic acid), or a single wound-healing agent that contains both antimicrobial and hemostatic activities (e.g., chitosan niacinamide ascorbate salt).

U.S. Pat. No. 6,891,077 to Rothwell et al. discloses fibrinogen bandages that include a procoagulant such as propyl gallate, gallic acid, or a derivative thereof. Optional ingredients such as thrombin or an antimicrobial agent may also be included.

International Patent Application Publication No. WO 97/28823 to New Generation Medical Corporation discloses a hemostatic bandage that contains powdered fibrinogen and thrombin adhered to a fibrous matrix with a viscous, non-aqueous adhesive such as a viscous polysaccharide, glycol, or petroleum jelly.

Another hemostatic textile is disclosed in U.S. Patent Publication No. 2007/0160653 to Fischer et al.

Virtually all of the processes described previously to control bleeding rely on a chemical interaction between blood and blood elements to stimulate the formation of a not indigenous to the normal process of hemostasis. The presence of these chemicals may have unintentional or prolonged side effects as the body attempts to absorb them during the healing process.

Other hemostatic chemicals may contain animal-derived products that could cause an inflammatory or immune response. Examples of commonly used animal-derived products are thrombin, chitosan, collagen, and the like.

Also, many of the previously mentioned hemostatic chemicals cause a blood clot to form which contains unwanted chemicals that the surgeon would prefer to remove from the surgical site to either help visualize the underlying wound or to reduce interference with subsequent wound healing.

Ultimately, the preferred method of controlling bleeding would be a device which enhances the body's own clotting processes, thereby accelerating the blood clotting cascade, and does so without unnaturally interacting with the blood by chemical means or by leaving some chemical elements within the blood clot for the body to deal with during the healing process.

The invention is believed to be an answer to that need.

SUMMARY OF THE INVENTION

It is known that various blood elements in the clotting cascade are attracted to various metals. A common method to help prevent a sudden hemorrhage in arteriovenous malformations ("AVM") involves the implantation of metallic microcoils, such as the Gianturco coil, to stimulate the formation of a blood clot.

Kim, T S et al wrote of the thrombogenicity of tungsten coils (Invest. Radiology 1998 July; 33(7):407-10). Thor, A. et al. and Hong separately wrote of their studies in which various blood elements critical to the clotting cascade are attracted to titanium (*Biomaterials*, 2007 February; 28(6): 966-74. Epub 2006 Nov. 13 and *Thromb Haemost*, 1999 July; 82(1):58-64. Titanium is a highly thrombogenic biomaterial: possible implications for osteogenesis).

However, to the inventor's knowledge no one has proposed the use of metals in bandages to help stimulate the formation of a blood clot.

In one aspect, disclosed herein is a hemostatic fabric, comprising a metal material in the form of fibers or metal powder, or combinations thereof; and one or more secondary fibers including but not limited to natural or synthetic, silk fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers, acetate fibers, and combinations thereof; the hemostatic fabric capable of activating hemostatic systems in the body when applied to a wound.

In another aspect, disclosed herein is a hemostatic fabric, comprising: a material comprising a combination of about 10% to 80% by weight metal fibers or metal powder, or combinations thereof; and about 20% to 90% by weight of one or more secondary fibers including but not limited to natural or synthetic, silk fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers, acetate fibers, and combinations thereof; the hemostatic fabric capable of activating hemostatic systems in the body when applied to a wound.

In yet another aspect, disclosed herein is a hemostatic fabric, comprising a material comprising metal fibers or metal powder, or combinations thereof; and one or more secondary fibers including but not limited to silk fibers; polyester fibers; nylon fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers; acetate fibers; and combinations thereof; and thrombin or a fraction comprising thrombin; the hemostatic fabric capable of activating hemostatic systems in the body when applied to a wound.

In yet another aspect, disclosed herein is a hemostatic fabric, comprising: a material comprising a combination of 10% to 80% by weight metal fibers or metal powder, or combinations thereof; and about 20% to 90% by weight of one or more secondary fibers of raw silk fibers; polyester fibers; nylon fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers; acetate fibers; and combinations thereof; and from about 0.1% to about 5% by weight of thrombin or a fraction comprising thrombin based on the total weight of the fabric; the hemostatic fabric capable of activating hemostatic systems in the body when applied to a wound.

In yet another aspect, disclosed herein is a hemostatic fabric, comprising: a material comprising metal fibers or metal powder, or combinations thereof; and one or more secondary fibers including but not limited to silk fibers; polyester fibers; nylon fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers; acetate fibers; and combinations thereof; and one or more hemostatic agents selected from the group consisting of platelets, blood cells; fibrin, and fibrinogen; the hemostatic fabric capable of activating hemostatic systems in the body when applied to a wound.

In yet another aspect, disclosed herein is a hemostatic fabric, comprising: a material comprising a combination of metal fibers or powder or combinations thereof; and one or more secondary fibers including but not limited to silk fibers; polyester fibers; nylon fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers; acetate fibers; and combinations thereof; and one or more hemostatic agents selected from the group consisting of platelets, blood cells, fibrin, and fibrinogen, wherein the hemostatic agents comprise from about 0.1% to about 20% weight of the total weight of the fabric; the hemostatic fabric capable of activating hemostatic systems in the body when applied to a wound.

Another aspect of the healing process is ensuring the nascent blood clot in a healing wound is not disturbed during the removal of any bandages. Fischer, et al disclosed the properties of bamboo fabric which help prevent a nascent blood clot from attaching to a bandage (T H Fischer et al., Biomed Mater Res Part B: Appl Biomater 91B:381-389, 2009).

In one aspect, disclosed herein is a hemostatic fabric, comprising a metal material in the form of fibers or metal powder, or combinations thereof; and secondary fibers of raw or regenerated bamboo fibers; the hemostatic fabric capable of activating hemostatic systems in the body when applied to a wound and, upon its removal, reduces the disruption of the blood clot and reduces the incidence or severity of adherence of the hemostatic fabric to the wound site.

In another aspect, disclosed herein is a hemostatic fabric, comprising: a material comprising a combination of about 10% to 80% by weight metal fibers or metal powder, or combinations thereof; and about 20% to 90% by weight of secondary fibers of raw or regenerated bamboo fibers; the hemostatic fabric capable of activating hemostatic systems in the body when applied to a wound and, upon its removal, reduces the disruption of the blood clot and reduces the incidence or severity of adherence of the hemostatic fabric to the wound site.

In another aspect, disclosed herein is a hemostatic fabric, comprising a metal material in the form of fibers or metal powder, or combinations thereof; and secondary fibers of raw or regenerated bamboo fibers; and thrombin or a fraction comprising thrombin; the hemostatic fabric capable of activating hemostatic systems in the body when applied to a wound and, upon its removal, reduces the disruption of the blood clot and reduces the incidence or severity of adherence of the hemostatic fabric to the wound site.

In another aspect, disclosed herein is a hemostatic fabric, comprising a metal material in the form of fibers or metal powder, or combinations thereof; and secondary fibers of raw or regenerated bamboo fibers; and thrombin or a fraction comprising thrombin; the hemostatic fabric capable of activating hemostatic systems in the body when applied to a wound and, upon its removal, reduces the disruption of the blood clot and reduces the incidence or severity of adherence of the hemostatic fabric to the wound site.

In another aspect, disclosed herein is a hemostatic fabric, comprising a metal material in the form of fibers or metal powder, or combinations thereof; and secondary fibers of raw or regenerated bamboo fibers; and from about 0.1% to about 5% by weight of thrombin or a fraction comprising thrombin based on the total weight of the fabric; the hemostatic fabric capable of activating hemostatic systems in the body when applied to a wound and, upon its removal, reduces the disruption of the blood clot and reduces the incidence or severity of adherence of the hemostatic fabric to the wound site.

In another aspect, disclosed herein is a hemostatic fabric, comprising a metal material in the form of fibers or metal powder, or combinations thereof; and secondary fibers of raw or regenerated bamboo fibers; and one or more hemostatic agents selected from the group consisting of platelets, blood cells; fibrin, and fibrinogen; the hemostatic fabric capable of activating hemostatic systems in the body when applied to a wound and, upon its removal, reduces the disruption of the blood clot and reduces the incidence or severity of adherence of the hemostatic fabric to the wound site.

These and other aspects will become apparent upon reading the following detailed description of the invention.

DETAILED DESCRIPTION OF THE PREFERRED EMBODIMENT

Figure 1:
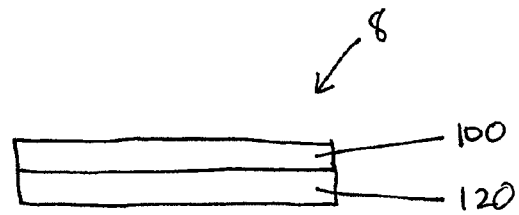
FIG. 1 illustrates schematically an end view of a hemostatic fabric according to one embodiment.

The inventor has found that a hemostatic fabric can be prepared from a composite of metal fibers or metal powder, or combinations thereof, and one or more secondary fibers. The hemostatic fabric made from the composite displays excellent hemostatic properties and fluid absorbency. To further enhance the hemostatic properties of the hemostatic fabric made from the composite, additional blood factors such as thrombin, lyophilized blood cells, lyophilized platelets, fibrin, fibrinogen, or combinations of these, may be added. These additional factors aid in activating the body's natural hemostasis cascade and result in a material that can rapidly arrest bleeding. The inventors have discovered that the combination of metal fibers, secondary fibers, and additional blood factors produce a novel hemostatic fabric that rapidly arrests bleeding, and is useful in situations where large hemorrhages exist or when a patient cannot be immediately admitted to a hospital or trauma treatment center.

In some embodiments, the hemostatic fabric provides important advantages over current products that activate hemostasis. For example, some embodiments are capable of rapidly activating the body's natural blood coagulation cascade by providing locally high concentrations of substances that activate that cascade. In addition, by using lyophilized blood proteins, the hemostatic fabric may be stored in a dry state ready for immediate use for long periods of time. This aspect is particularly advantageous because previous products and systems required hydrated proteins for activation.

As indicated above, one embodiment is a hemostatic fabric matrix, comprising a material comprising a combination of metal fibers or metal powder or combinations thereof and one or more secondary fibers. Each of these components is discussed in more detail below.

The metal fiber component can include a metal prepared by extrusion or electrospinning processes, and has fiber diameters from, for example, 5 nanometers to 15 microns. Types of metals contemplated for use in certain embodiments as disclosed herein include but are not limited to steel (e.g., stainless steel), tungsten, titanium, and platinum. Other possible metals could include, for example, tantalum, gold, palladium, silver, nickel, cobalt, copper, or chromium. The metals can be alloys, such as Nitinol or Elgiloy, and can be combinations of metals. In some embodiments, the combination could include at about or least about 5%, 10%, 20%, 30%, 40%, 50%, 60%, 70%, 80%, 90%, or more of a first metal and no more than about or about 90%, 80%, 70%, 60%, 50%, 40%, 30%, 20%, 10%, 5%, or less of a second metal. In addition, strand count of the metal fiber component can range from, for example, from 900 to 37. The metal fibers may also be used singly or in a plied state using 2 to 20 or more fibers, for example.

Metal powders (including nanoparticles) can be used with metal fibers, or can be used alone with the secondary fibers. The metal powders can be applied to a special prepared fiber to strongly bond with the metal powder and then woven or combined with the secondary fibers, or the metal powders can be bonded directly to the secondary fibers chemically or magnetically. Types of metal powders contemplated for use with certain embodiments disclosed herein include but are not limited to steel (e.g., stainless steel), tungsten, titanium, and platinum. Other possible metals could include, for example, tantalum, gold, palladium, silver, nickel, cobalt, copper, or chromium. The metals can be alloys, such as Nitinol or Elgiloy. The metal powders can also be combinations of various metals. In some embodiments, the combination could include at about or least about 5%, 10%, 20%, 30%, 40%, 50%, 60%, 70%, 80%, 90%, or more of a first metal and no more than about or about 90%, 80%, 70%, 60%, 50%, 40%, 30%, 20%, 10%, 5%, or less of a second metal. The powders can be applied to the fibers by commercially available processes such as vapor deposition, sputtering, spraying, or evaporating.

Secondary fibers used in fabric of some embodiments include generally any other fiber that can be combined with the metal fibers to impart absorbency, softness, and additional hemostatic activity to the fabric. The secondary fibers mayor may not be absorbable. As explained in more detail below, use of secondary fibers with excellent absorbency also aids in incorporating additional hemostatic factors to the fabric. Examples of useful secondary fibers include, but are not limited to, silk fibers; polyester fibers; nylon fibers; ceramic fibers; polysaccharide fibers including plant fibers such as raw or regenerated (e.g., chemically processed) bamboo, cotton, rayon, linen, ramie, jute, sisal, flax, soybean, corn, hemp, and lyocel; animal fibers such as wool; lactide and/or glycolide polymers; lactide/glycolide copolymers; silicate fibers; polyamide fibers; feldspar fibers; zeolite fibers, zeolite-containing fibers; acetate fibers; plant fibers that have been genetically engineered to express mammalian coagulation proteins or mammalian vasoactive factors. Other secondary fibers that are suitable for use are fibers that have been covalently modified with polymers to promote water absorbancy (e.g., polyvinyl alcohols) and polymers that contain molecular moieties that activate hemostatic systems (e.g., linear or cyclized-arginine-glycine-aspartate moieties such as those found in eptifibatide). Preferred secondary fibers include plant fibers such as raw or regenerated (e.g., chemically processed) bamboo fibers, cotton fibers, and the like, that have high moisture absorbancy and that are capable of activating the intrinsic coagulation cascade. The secondary fibers may be prepared using conventional methods, including ring, open end (OE), rotor, or air jet spinning, and may have counts ranging from 1/1 to 100/1 Ne.

In some, embodiments, the secondary fibers may by, used singly, or in combinations of two, three, four, or more in a blended or plied state. In addition, any type of combination of secondary fibers may be used, including natural fibers, synthetic fibers, or both. For example, in one embodiment, two or more secondary fibers may be individually produced and then blended or plied together to form a composite yarn. In another embodiment, the secondary fibers may be formed as a conjugate comprising blocks of the selected types of fibers, for example alternating blocks of polyesters and polysaccharides. In yet another embodiment, the secondary fibers may be formed as a homogeneous combination of different, threads.

The relative amounts of metal fibers and secondary fibers can range widely, for example from about 0.1 to 99.9 wt % metal fibers and about 99.9% to 0.1% by weight secondary fibers, based on the total weight of the dried fabric. Some embodiments include amounts of these materials that range from about 30 to 80 wt % metal fibers and about 70 to 20 wt % secondary fibers, and sometimes from about 50 to 80 wt % metal fibers to about 50 to 20 wt % secondary fibers. Nonlimiting examples of useful proportions of metal and secondary fibers in the hemostatic fabric include about 50 wt % metal fibers and about 50 wt % secondary fibers; about 40 wt % metal fibers and about 60 wt % secondary fibers; about 30 wt % metal fibers and about 70 wt % secondary fibers; or about 20 wt % metal fibers and about 80 wt % secondary fibers. One particular combination is about 65% by weight metal fibers and 35% by weight bamboo fibers. The metal fiber component and the secondary fiber component, may be combined using conventional methods such as spinning, weaving or knitting, or may be used in a nonwoven state.

In use, the hemostatic fabric may take any configuration. In one embodiment, the hemostatic fabric includes a first layer, e.g., a hemostatic layer designed to accelerate hemostasis, and a second layer (e.g., an outer layer) designed for surface texture, moisture transfer, fluid adsorption and microbial protection. In another embodiment, the hemostatic fabric includes three layers: a first hemostatic layer designed to accelerate hemostasis, a second, e.g., a middle layer for bandage strength and elasticity, and a third, e.g., an outer layer for designed for surface texture, moisture transfer, fluid adsorption and microbial protection. Additional configurations or combinations are also within the scope of the invention.

FIG. 1 schematically illustrates an end view of a hemostatic fabric 8, according to one embodiment. The fabric 8 includes a first hemostatic layer 100 that may include metal fibers or powder, and a second layer 120 including natural or synthetic fibers.

Figure 2:
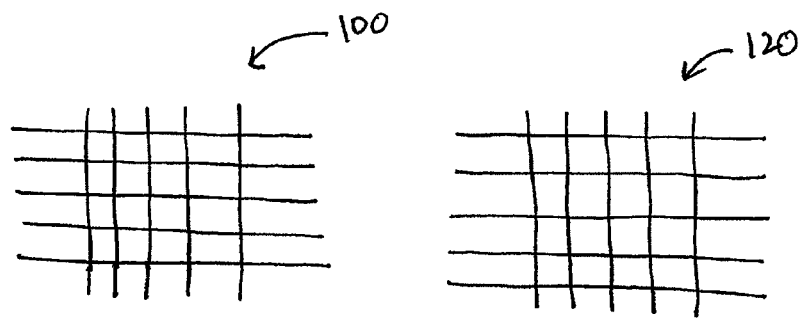
FIG. 2 illustrates schematically an exploded view showing a first hemostatic layer and a second layer, as previously described.

FIG. 2 illustrates schematically an exploded view showing a first hemostatic layer 100 and a second layer 120 as previously described.

Figure 3:
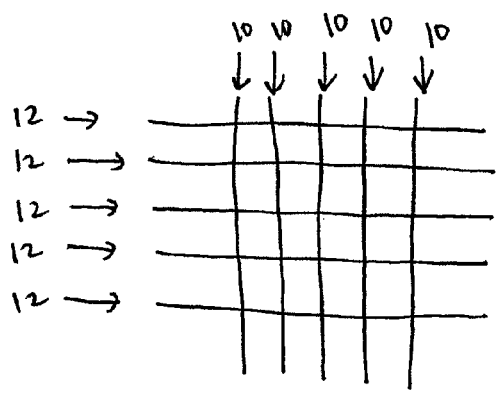
FIG. 3 illustrates a layer of a hemostatic fabric, including a first number of hemostatic fibers generally travelling in a first direction, and a second number of fibers generally travelling in a second direction, according to some embodiments.

FIG. 3 illustrates a layer of a hemostatic fabric, including a first number of hemostatic fibers 10 generally travelling in a first direction, and a second number of fibers 12 generally travelling in a second direction, according to some embodiments.

Figure 4:
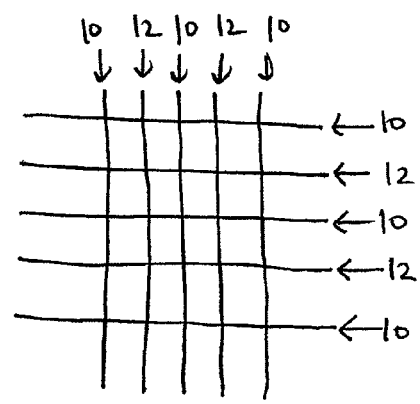
FIG. 4 illustrates a layer of hemostatic fabric, including interspersed hemastatic fibers and other natural or synthetic fibers. A number of other fiber patterns and manner in which fibers are intertwined can also be used, depending on the desired clinical result.

FIG. 4 illustrates a layer of hemostatic fabric, including interspersed hemostatic fibers 10 and other natural or synthetic fibers 12. A number of other fiber patterns and the manner in which fibers are intertwined can also be used depending on the desired clinical result.

The hemostatic fabric may also be treated with various agents that enhance its effectiveness. Examples of additional agents include organic or inorganic compounds that are micro static or microcidal; organic or inorganic compounds that covalently react with blood coagulation proteins; organic or inorganic compounds that covalently react with wounded tissue to form covalent bonds for enhanced adhesion to tissues; organic or inorganic compounds that polymerize to form a three-dimensional polymer network at or on the wound; imaging agents such as ultrasound contrast agents (e.g., gas-filled microbubbles, metallic nanoparticles, and the like), radio-opaque agents (e.g., iodinated small molecules such asiopromide, iodinated high molecular weight polymers, and the like), magnetic resonance probes (e.g., ferumoxide iron nanoparticles, superparamagnetic metallic nanoparticles, diethylenetriaminepentaacetate (DTP A)-chelated gadolinium, and polymers that contain DTPA-chelated gadolinium, and the like).

Further additional agents that may be included in the hemostatic fabric include skin conditioners such as aloe vera, vitamin E, coenzyme Q, collagen, and the like; anti-inflammatory agents such as aspirin, ibuprofen, acetaminophen, vitamin C, COX-2 inhibitors, steroids, and the like; analgesics such as lidocaine, tetrocaine, opiates, cocaine, antihistamines, and the like; antimicrobial or antifungal agents such as bacitracin, silver salts, iodide, and the like; vasoconstrictors such as epinepherine, norepinephrine, vasopressin, cocaine compounds, hemoglobin, endothelins, thromboxanes, NO scavengers, and the like; growth factors such as MMP inhibitors, PDGF, and the like; anti-scar agents such as IL-11, anti-keloid compounds, and the like; cauterizing agents; dehydrating agents; prothrombotic agents, such as zeolite, dextran sulfate, polyphosphate, mineral interfaces, phosphatidyl serine, calcium, and the like.

The fabric matrix may also include additional factors that act to activate the body's natural hemostatic processes and thus aid in quickly arresting bleeding. Such additional factors include thrombin or a plasma fraction that includes thrombin, platelets, blood cells, fibrin, fibrinogen, and combinations of these.

In one preferred embodiment, thrombin is incorporated into the fabric to impart additional hemostatic action. The thrombin can be from any source (naturally isolated, recombinant, etc.) or may be in the form of a plasma fraction or serum that contains thrombin and additional coagulation factors such as factor XII, factor XIIa, factor XI, factor XIa, factor XIII, factor XIIIa, factor IX, factor IXa, factor VIII, factor VIIIa, factor vWF, factor V, factor Va, factor X, factor Xa, and combinations thereof, or other coagulation cofactors such as components of animal venom, such as reptilase, or vasoactive agents such as endothelins, thromboxanes, nitrous oxide (NO) scavengers, fibrinogen, fibrin, or combinations thereof.

The hemostatic fabric would be packaged sterile for single use and could be offered in a variety of sizes and configurations. One configuration would be in flat square, rectangular, or round patches ranging in size from 2 cm by 2 cm to 30 cm by 30 cm, for example. Another configuration would be in patches that rolled or folded sufficiently to fit through a trocar or other less invasive port to a surgical site. Another configuration would be similar to a ball in shape and fixed to the tip of a probe, applicator, or endoscope to fit into such small spaces as the nose (e.g. a nose bleed) or ear, gastrointestinal tract, such as to treat esophageal varices, or other body lumens or difficult to reach bleeding sites. The hemostatic fabric could be used to treat, prevent, or ameliorate bleeding at any site within the body, for example, to stop cutaneous bleeding, soft tissue bleeding; vascular organs such as the liver, spleen, pancreas, lungs, heart, stomach, bladder, ovaries, uterus, or cervix, and the like.

The hemostatic fabric may contain one or more adhesive agents or be attached to an adhesive material to assist or enable the patch to remain on a bleeding wound site. The hemostatic fabric may contain one or more radiopaque threads to assist in locating a lost patch in a closed wound site.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A hemostatic fabric consisting of:
   at least one selected from the group consisting of: a metal thread, a metal powder, and a combination thereof configured to stimulate the formation of a blood clot; and
   a secondary fabric consisting of at least one of natural or synthetic fibers to support and accelerate hemostasis.

2. The hemostatic fabric of claim 1, wherein the metal thread, metal powder, or combination thereof comprises steel.

3. The hemostatic fabric of claim 1, wherein the metal thread, metal powder, or combination thereof comprises tungsten.

4. The hemostatic fabric of claim 1, wherein the metal thread, metal powder, or combination thereof comprises titanium.

5. The hemostatic fabric of claim 1, wherein the metal thread, metal powder, or combination thereof comprises platinum.

6. The hemostatic fabric of claim 1, wherein the metal thread, metal powder, or combination thereof comprises silver.

7. The hemostatic fabric of claim 1, wherein the metal thread, metal powder, or combination thereof comprises tantalum.

8. The hemostatic fabric of claim 1, wherein the metal thread, metal powder, or combination thereof comprises palladium.

9. The hemostatic fabric of claim 1, wherein the metal thread, metal powder, or combination thereof comprises a metallic alloy.

10. The hemostatic fabric of claim 1, wherein the secondary fabric comprises antimicrobial properties to reduce or control infectious agents.

11. A method of achieving hemostasis in a patient, comprising:
    providing a hemostatic fabric consisting of at least one selected from the group consisting of: a metal thread, a metal powder, and a combination thereof; and a secondary fabric consisting of at least one of natural or synthetic fibers to reduce the adherence of the hemostatic fabric to the wound;
    identifying a site of the patient where there is bleeding; and
    stimulating formation of a blood clot, wherein stimulating formation of a blood clot comprises positioning the hemostatic fabric at the site of bleeding.

12. A hemostatic fabric, consisting of:
    at least one selected from the group consisting of: a metal thread, a metal powder, and a combination thereof configured to stimulate the formation of a blood clot; and
    a secondary fabric comprising at least one of natural or synthetic fibers to reduce the adherence of the hemostatic fabric to the wound,
    wherein the secondary fabric does not comprise any additional hemostatic materials.

* * * * *